(12) United States Patent
Anderson et al.

(10) Patent No.: US 11,123,042 B2
(45) Date of Patent: Sep. 21, 2021

(54) AUTOMATED THREE AND FOUR-DIMENSIONAL ULTRASOUND QUANTIFICATION AND SURVEILLANCE OF FREE FLUID IN BODY CAVITIES AND INTRAVASCULAR VOLUME

(71) Applicant: The Government of the United States as Represented by the Secretary of the Army, Fort Detrick, MD (US)

(72) Inventors: Shane B. Anderson, Salt Lake City, UT (US); Lorne H. Blackbourne, Austin, TX (US); Mariya Gusman, St. Louis, MO (US); Jose Salinas, Fort Sam Houston, TX (US)

(73) Assignee: The Government of the United States as Represented by the Secretary of the Army, Ft. Detrick, MD (US)

( * ) Notice: Subject to any disclaimer, the term of this patent is extended or adjusted under 35 U.S.C. 154(b) by 321 days.

(21) Appl. No.: 16/315,543

(22) PCT Filed: Aug. 10, 2017

(86) PCT No.: PCT/US2017/046264
§ 371 (c)(1),
(2) Date: Jan. 4, 2019

(87) PCT Pub. No.: WO2018/031754
PCT Pub. Date: Feb. 15, 2018

(65) Prior Publication Data
US 2019/0254633 A1 Aug. 22, 2019

Related U.S. Application Data

(60) Provisional application No. 62/373,028, filed on Aug. 10, 2016.

(51) Int. Cl.
*A61B 8/08* (2006.01)
*A61B 8/00* (2006.01)
(Continued)

(52) U.S. Cl.
CPC .............. *A61B 8/483* (2013.01); *A61B 8/466* (2013.01); *A61B 8/5223* (2013.01);
(Continued)

(58) Field of Classification Search
CPC ....... A61B 8/483; A61B 8/466; A61B 8/5223; A61B 5/02007; A61B 8/04; A61B 8/06;
(Continued)

(56) References Cited

U.S. PATENT DOCUMENTS 6,368,286 B1 4/2002 Whitman et al.
6,514,208 B1 2/2003 Cancio et al.
(Continued)

FOREIGN PATENT DOCUMENTS

CA 2845044 A1 2/2013
WO 1993021827 A1 11/1993
(Continued)

OTHER PUBLICATIONS

Kim et al., Usefulness of Renal Volume Measurements Obtained by a 3-Dimensional Sonographic Transducer With Matrix Electronic Arrays, 2018, American Institute of Ultrasound in Medicine, 27:1673-1681 (Year: 2008).*
(Continued)

*Primary Examiner* — Keith M Raymond
*Assistant Examiner* — Andrew W Begeman
(74) *Attorney, Agent, or Firm* — Leigh Callander (57) ABSTRACT

An embodiment of the invention provides a method to measure fluid within a body cavity where data is received with an interface (210), the data being received from an ultrasound transducer. A three-dimensional sonographic
(Continued)

image is generated with an image generator (220) connected to the interface (210), the three-dimensional sonographic image being generated from the data from the ultrasound transducer. The body cavity is identified in the three-dimensional sonographic image with an image processor (230) connected to the image generator (220); and, an area of fluid in the body cavity in the three-dimensional sonographic image is identified with the image processor (230). The volume of the area of fluid is calculated using the three-dimensional sonographic image and a stacked crescents process, a spherical fill process, a convex hull process, and/or a triangulation process.

14 Claims, 6 Drawing Sheets (51) Int. Cl.
| | | |
|---|---|---|
| A61B 8/06 | (2006.01) | |
| G16H 30/40 | (2018.01) | |
| A61B 5/02 | (2006.01) | |
| A61B 8/04 | (2006.01) | |

(52) U.S. Cl.
CPC .............. *A61B 5/02007* (2013.01); *A61B 8/04* (2013.01); *A61B 8/06* (2013.01); *G16H 30/40* (2018.01)

(58) Field of Classification Search
CPC ........ A61B 8/085; A61B 8/406; G61H 50/30; G16H 30/40
See application file for complete search history.

(56) References Cited

U.S. PATENT DOCUMENTS

| | | | |
|---|---|---|---|
| 6,650,924 | B2 | 11/2003 | Kuth et al. |
| 7,920,731 | B2 | 4/2011 | Moreau-Gobard et al. |
| 8,167,803 | B2 | 5/2012 | McMorrow et al. |
| 8,394,031 | B2 | 3/2013 | Mansy et al. |
| 8,454,516 | B1 | 6/2013 | Roundhill et al. |
| 2004/0081340 | A1 | 4/2004 | Hashimoto |
| 2005/0124885 | A1 | 6/2005 | Abend et al. |
| 2007/0019846 | A1 | 1/2007 | Bullitt et al. |
| 2007/0066895 | A1 | 3/2007 | Sikdar et al. |
| 2008/0146932 | A1 | 6/2008 | Chalana et al. |
| 2008/0183077 | A1 | 7/2008 | Moreau-Gobard et al. |
| 2008/0234567 | A1 | 9/2008 | Tearny et al. |
| 2009/0149748 | A1 | 6/2009 | Lenhardt et al. |
| 2009/0177092 | A1 | 7/2009 | Riechers et al. |
| 2010/0222663 | A1 | 9/2010 | Wilder et al. |
| 2010/0274130 | A1 | 10/2010 | Anand et al. |
| 2012/0016240 | A1 | 1/2012 | Lee et al. |
| 2013/0018240 | A1 | 1/2013 | McCoy |
| 2013/0197370 | A1 | 8/2013 | Burlina et al. |
| 2014/0213901 | A1 | 7/2014 | Shackelford |
| 2016/0239959 | A1 | 8/2016 | Grisell et al. |
| 2018/0303459 | A1* | 10/2018 | Walton ............... A61B 8/06 |
| 2019/0066298 | A1* | 2/2019 | Snook .............. H01Q 1/1214 |

FOREIGN PATENT DOCUMENTS

| | | |
|---|---|---|
| WO | 9858588 A1 | 12/1998 |
| WO | 2008073560 A3 | 6/2008 |
| WO | 2015048767 A1 | 4/2015 |

OTHER PUBLICATIONS

Kristiansen et al., Design and evaluation of an ultrasound-based bladder volume monitor, 2004, Medical & Biological Engineering & Computing, vol. 42 (Year: 2004).*

Dhibi et al., Volume Calculation of Venous Thrombosis Using 2D ultrasound images, 2005, Engineering in Medicine and Biology 27th Annual Conference (Year: 2005).*

Deng et al., Quantitative Assessment of Variational Surface Reconstruction from Sparse Point Clouds in Freehand 3D Ultrasound Imaging during Image-Guided Tumor Ablation, Apr. 19, 2016, Applied Sciences MDPI (Year: 2016).*

Helen Morehouse, et al. Addition of Metamucil to Gelatin for a Realistic Breast Biopsy Phantom. American Institute of Ultrasound in Medicine. J Ultrasound Med 2007; 26:1123-1126.

James M. Gebel, et al. Comparison of the ABC/2 Estimation Technique to Computer-Assisted Volumetric Analysis of Intraparenchymal and Subdural Hematomas Complicating the GUSTO-1 Trial. Stroke. 1998:29:1799-1801.

Kasne, et al.: Geometry and Subdural Hematoma Volume. Stroke:1999:30:Issue 1.

International Search Report and Written Opinion of the International Search Authority for PCT/US2017/046264, dated Oct. 19, 2017.

Lichtenstein et al.: "Ultrasound diagnosis of occult pneumothorax*", Crit Care Med, 2005. p. 1231-1238.

Testa, et al.: "Psychiatric emergencies (part III): psychiatric symptoms resulting from organic diseases", European Review for Medical and Pharmacological Sciences, Feb. 17, 2013 (Supp b1). p. 86-99.

Soldati, et al.: "The ultrasonographic deep sulcus sign in traumatic pneumothorax", Ultrasound in Med. & Biol., vol. 32, No. 8, 2006. p. 1157-1163.

International Search Report and Written Opinion for PCT/US2014/058374, dated Feb. 1, 2015 entire document.

Chan, et al.: Emergency Bedside Ultrasound to Detect Pneumothorax, Academic Emergency Medicine, Jan. 2003, pp. 91-94, 10-1.

Perera, et al.: "The RUSH Exam: Rapid Ultrasound in SHock in the Evaluation of the Critically Ill," Emergency Medicine Clinic North America, 2010, pp. 29-56, 28, Elsevier.

Gu, et al.: "Efficacy of Ultrasound-Guided Radial Artery Catheterization": a systematic review and meta-analysis of randomized controlled trials. Critical Care 2014, 18:R93. p. 1-7

Ueda K, et al.: "Ultrasound Visual Image-Guided-vs-Doppler Auditory-Assisted Radial Artery Cannulation in infants and small children by non-expert Anaesthesiologists": a randomized prospective study. Br. J. Anaesth 2013, 110:281-286.

Froehlich, et al.: "Ultrasound-Guided Central Venous Catheter placement decreases complications and decreases placement attempts compared with the landmark technique in patients in a pediatric intensive care unit": Critical Care Medicine. 2009 vol. 37, No. 3. pp. 1090-1096.

Calvert, et al.: "Ultrasound for Central Venous Cannulation" Economic Evaluation of Cost-Effectiveness. Anaesthesia, 2004, 59: pp. 1116-1120.

Tsai, et al.: "Ring Down Artefacts on Abdominal Sonography to Predict Pulmonary Abnormalities in the Emergency Department." Emerg Med J, 22, 2005, pp. 747-748.

Kline, et al.: Detection of Pneumothorax with Ultrasound. AANA Journal, vol. 81, No. 4, Aug. 2013, pp. 265-271.

Brooke M, et al.: Paramedic application of ultrasound in the management of patients in the prehospital setting. A review of the Literature. Emeg Med J. 27(9):702-707.2010. (Abstract).

Heegaard W, et al.: Prehospital Ultrasound by Paramedics: Results of Field Trial. Society for Academic Emergency Medicine. 2010. vol. 17(6):624-630. (Abstract).

Hile DC, et al.: Is Point-of-Care Ultrasound Accurate and Useful in the Hands of Military Medical Technicians? A Review of the Literature. Military Medicine. 2012. 177(8):983-987.

Holcomb J, et al.: Causes of Death in U.S. Special Operations Forces in the Global War on Terrorism 2001-2004. Annuals of Surgery. 245:986-991.

El Sayed MJ, et al.: Prehospital Emergency Ultrasound: A Review of Current Clinical Applications, Challenges, and Future Implications. Emergency Medical International. 2013. pp. 1-7

Chin EJ, et al.: A Pilot Study Examining the Viability of a Prehospital Assessment with Ultrasound for Emergencies (PAUSE) Protocol. The Journal of Emergency Medicine. 2013. 44(1):142-149.

(56) References Cited

OTHER PUBLICATIONS

Lyon M, et al.: M-mode Ultrasound for the Detection of Pneumothorax During Helicopter Transport. The American Journal of Medicine. vol. 30(8):1577-80. Oct 2012. (Abstract).
Stawicki SP, et al.: Portable Ultrasonography in Mass Casualty Incidents: The CAVEAT Examination. World Journal of Orthopedics. 1(1):10-19. 2010.

* cited by examiner

AUTOMATED THREE AND FOUR-DIMENSIONAL ULTRASOUND QUANTIFICATION AND SURVEILLANCE OF FREE FLUID IN BODY CAVITIES AND INTRAVASCULAR VOLUME

This application is a national stage application of PCT international application PCT/US2017/046264 filed on Aug. 10, 2017, which claims benefit of U.S. Patent Application Ser. No. 62/373,028 filed on Aug. 10, 2016, the entirety of each which is herein incorporated by reference.

FIELD OF INVENTION

The present invention relates to systems, methods, and computer program products for automated three and four-dimensional ultrasound quantification and surveillance of free fluid in body cavities and intravascular volume.

BACKGROUND

In the trauma setting, free fluid is presumed to represent blood and its presence is abnormal. This is the basis of the Focused Assessment with Sonography for Trauma (FAST) examination. The current state of the art in the sonographic detection of free fluid requires trained operators, who typically utilize two-dimensional (B-mode) images acquired in transverse and longitudinal planes. The operator determines whether fluid is present by visually analyzing the two-dimensional images to determine the presence of hypoechoic collections which would be consistent with free fluid.

SUMMARY OF THE INVENTION

An embodiment of the invention provides a method to measure fluid within a body cavity where data is received with an interface, the data being received from an ultrasound transducer. A three-dimensional sonographic image is generated with an image generator connected to the interface, the three-dimensional sonographic image being generated from the data from the ultrasound transducer. The body cavity is identified in the three-dimensional sonographic image with an image processor connected to the image generator; and, an area of fluid in the body cavity in the three-dimensional sonographic image is identified with the image processor. The volume of the area of fluid is calculated using the three-dimensional sonographic image and a stacked crescents process, a spherical fill process, a convex hull process, and/or a triangulation process.

Another embodiment of the invention provides a system to measure fluid within a body cavity, where the system includes an interface configured to receive data from an ultrasound transducer. An image generator is connected to the interface and is configured to generate a three-dimensional sonographic image from the data from the ultrasound transducer. An image processor is connected to the image generator and is configured to identify the body cavity in the three-dimensional sonographic image. The image processor is also configured to identify the area of fluid in the body cavity in the three-dimensional sonographic image. The image processor calculates the volume of the area of fluid using the three-dimensional sonographic image and a stacked crescents process, a spherical fill process, a convex hull process, and/or a triangulation process.

BRIEF DESCRIPTION OF THE DRAWINGS

The present invention is described with reference to the accompanying drawings. In the drawings, like reference numbers indicate identical or functionally similar elements.

DETAILED DESCRIPTION

Non-limiting embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

At least one embodiment of the invention provides a device and algorithm to measure fluid (e.g., blood) within body cavities using a three-dimensional sonographic image derived from an (or multiple) ultrasound transducer. The method in at least one embodiment of the invention includes, but is not limited to, for example the measurement of fluid within perihepatic, perisplenic, or intravascular spaces (e.g., inferior vena cava).

Specifically, in at least one embodiment, the system utilizes automated volume acquisition with subsequent analysis of the volumetric data set to perform segmentation and determination of segmented volumes using an algorithm. Using different volumetric analysis techniques, an accurate measurement of a fluid volume contained within an irregular space can be determined.

The automated detection of volume allows for monitoring over time in order to alert providers of increasing free fluid volume or changes in intravascular volume. Examples of transducers that could be used in the system include: a two-dimensional transducer used to sweep across an anatomic volume (region) of interest with the resulting sequential frames integrated into a three-dimensional volume data set representation; an automated transducer sweep acquisition of a three-dimensional volume; a recurrent automated sweep acquisition of the same volume to calculate changes over time (four-dimensional—i.e. dynamic or recurrent three-dimensional acquisitions); and/or numerous integrated sensors spread over space within a flexible material serving as a transducer, acquiring volumetric data sets, which are then further integrated via post-processing to create a larger volume set.

Potential volume definition (segmentation) methods include: a semi-automated x/y/z plane region of interest where a user outlines a region of interest (ROI) on at least three orthogonal planes with interface detection completing the definition of the volume of interest; a semi-automated single plane region of interest where a user outlines a region of interest on sequential parallel planes, which are then integrated (the greater the sensitivity for interface, the fewer planes required); a semi-automated single point where a user indicates point of interest (POI) on single plane, the boundaries of the hypoechoic region associated with this point are detected in three planes and volume is defined; and/or an automated detection of hypoechoic region, where software automates detection of hypoechoic region by segmenting and summing confluent hypoechoic (dark) pixels/voxels in acquired images/volumetric data sets. Reference to anatomic location to improve sensitivity.

In at least one embodiment, vascular detection and identification of adjacent veins and arteries can be differentiated by wall thickness (arteries thicker), wall collapsibility (veins compress more readily with pressure), Doppler direction of flow (arteries away from heart/veins toward heart), and/or Doppler waveform (distinct waveforms, velocities and resistive indices). Anatomical atlas data are referenced to identify vessel and branch. This allows for identification of vessels which have been disrupted or contain thrombus (no flow, altered flow).

Intrathoracic/Intraperitoneal/Retroperitoneal Fluid Detection and Definition: Region of interest boundaries determined by differences in echogenicity between fluid and more echogenic material such as organ parenchyma. Acute fluid collections tend to be hypoechoic. As blood products age and clot, collections may become complex. In this scenario, pre-programmed targeting of adjacent organs is planned to improve targeting. Solid organs have distinct textures and shapes, and reference to a database thereof can reduce the chance that a portion of an organ is inadvertently incorporated into a fluid region of interest.

Potential Volume Calculation: Stacked Crescents (similar to stacked ellipses) wherein a crescent is the non-overlapping area of two partially overlapping circles. Serial crescentic areas are then summed for volume. Stacked Ellipse Crescents: Elongated, shortened, or otherwise irregular crescents can be generated with overlapping ellipsoids. In a spherical fill process, segmented volume approximated with the smallest number of spheres required to fill the contours of the volume. In at least one embodiment, large sphere centrally, smaller, partially exophytic spheres peripherally as needed. Spheres permitted to overlap, with overlapping volumes subtracted from total volume of spheres used. In at least one embodiment, convex hull (3D convex hull) algorithms provide a computation of the minimum convex sets that contain all the points in the region and/or volume. In at least one embodiment, delaunay triangulation (and minimum spanning tree) algorithms compute the minimum number of triangles that make up the Euclidian space of the points within the volume.

The system can be constructed with or without a display. A display would be required for semi-automated techniques, to allow for ROI/POI selection, whereas a fully automated system could be made smaller by omitting this component. The system can be provided with or without separation of the transducer and housing. The system can include a transducer (piezo components), power source, logic board, housing, and output interface (e.g., numerical indicator of size of fluid collection in fluid volume units). The components may or may not be separated by a cord, depending on which yields smallest overall device size.

Previous Focused Assessment with Sonography for Trauma (FAST) examinations are performed and interpreted by an individual with advanced medical training. The system in at least one embodiment automates this examination such that assessment could be performed by an individual with minimal training. The previous FAST examination can utilize two-dimensional ultrasound, whereas the present system utilizes three-dimensional ultrasound which is more accurate. The system allows for monitoring of free fluid collections and intravascular volume. The system can permit quantification of rate of internal hemorrhage and intravascular volume changes.

The system automates FAST examinations and quantifies the volume of free fluid. Quantifying increasing fluid volume over time would allow for assessment of interval change to optimize treatment. The system in at least one embodiment provides hemothorax detection, quantification and monitoring; Hemoperitoneum detection, quantification and monitoring; subcapsular hematoma detection (e.g., liver, spleen, kidney), quantification and monitoring; retroperitoneal hematoma detection, quantification and monitoring; and/or automated volume status assessment and monitoring. In the setting of trauma resuscitation, the system provides vascular targeting.

The system provides automated three and four-dimensional ultrasound imaging (X axis, Y axis, Z axis, and time) for hemorrhage detection and monitoring. The system can monitor the neck (e.g., internal Jugular vein, Carotid artery), abdomen (e.g., inferior vena cava) and/or groin (e.g., femoral vein and arteries). The system can provide automated volume calculation for three-dimensional crescentic fluid collections (e.g., subcapsular hematomas) using stacked crescents and/or subtraction of overlapping ellipsoid volumes.

Figure 1:
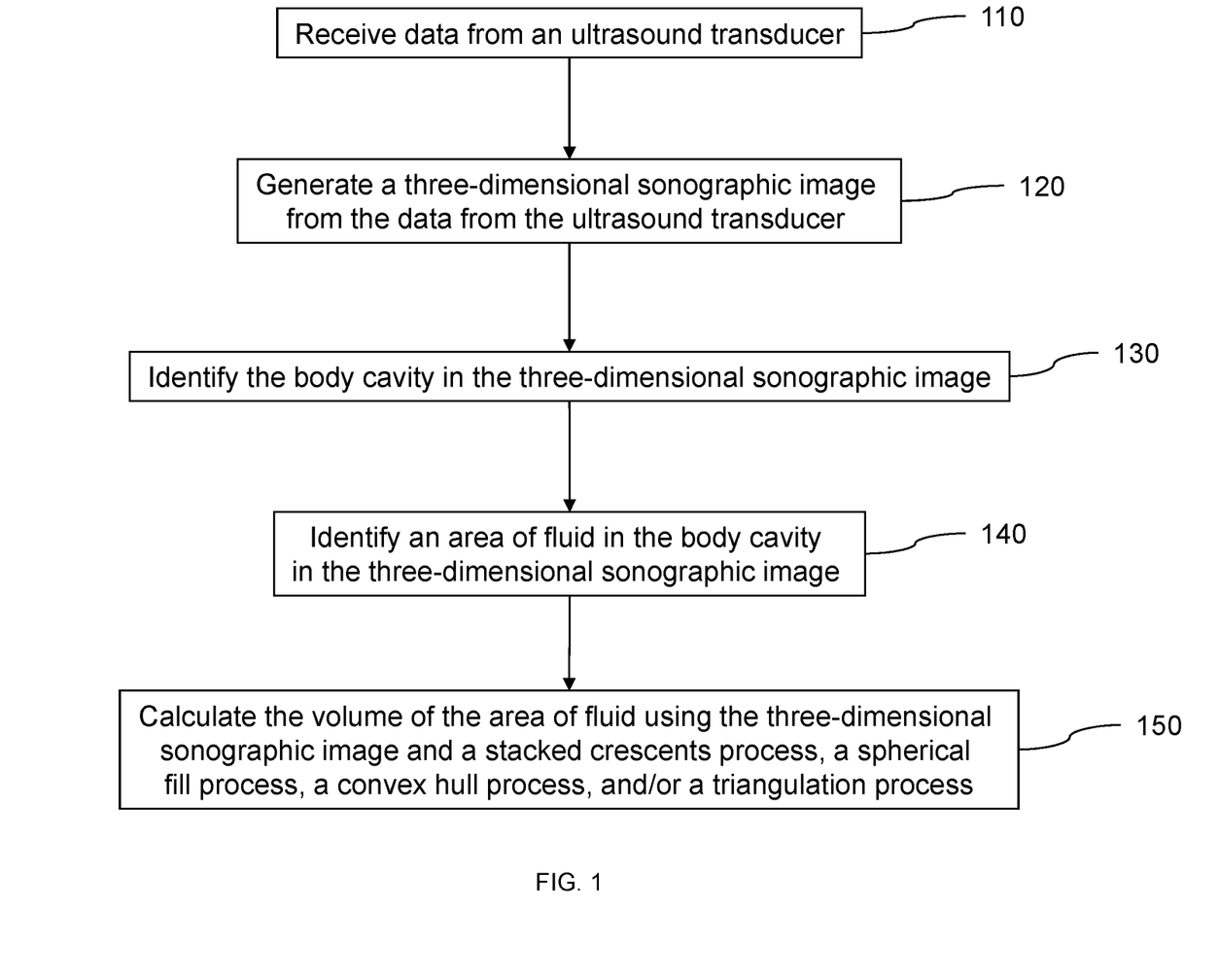
FIG. 1 is a block diagram illustrating a method to measure fluid within a body cavity and calculate rate of bleeding according to an embodiment of the invention.

FIG. 1 is a block diagram illustrating a method to measure fluid within a body cavity according to an embodiment of the invention. An interface can receive data from an ultrasound transducer 110. As used herein, the term "interface" includes a computer hardware device, such as, for example, a keyboard, a mouse, a microphone, a touchpad, a touchscreen, a joystick, a controller, a camera, a disk drive, an input port, antenna, etc. An image generator connected to the interface can generate a three-dimensional sonographic image from the data from the ultrasound transducer 120. As used herein, the term "image generator" includes a computer hardware device, such as, for example, a central processing unit (CPU), an integrated circuit, or a microprocessor. If additional scans of the same area (fluid collection) are performed, then the device notes the time of the serial scans and calculates (change in volume)/(change in time) to provide an estimated rate of hemorrhage.

An image processor connected to the image generator can identify the body cavity in the three-dimensional sonographic image 130. The image processor can identify an area of fluid in the body cavity in the three-dimensional sonographic image 140. The image processor can also calculate the volume of the area of fluid 150. The volume of the area of fluid can be calculated using the three-dimensional sonographic image and a stacked crescents process, a spherical fill process, a convex hull process, a triangulation process, and/or summation of segmented pixels. When summation of segmented pixels is used to calculate volume, the system automates the detection of a hypoechoic region by segmenting and summing confluent hypoechoic (dark) pixels/voxels in acquired images/volumetric data sets.

The stacked crescents process can include dividing the area of fluid in the three-dimensional sonographic image into stacked segments; identifying crescents in the three-dimensional sonographic image, wherein each crescent is a non-overlapping area of two partially overlapping segments; calculating an area of each crescent; and summing the areas of the crescents.

The spherical fill process can include virtually filling the area of fluid in the three-dimensional sonographic image with virtual spheres having a uniform volume; identifying a minimum number of virtual spheres required to fill the area of fluid in the three-dimensional sonographic image; and multiplying the number of virtual spheres required to fill the area of fluid in the three-dimensional sonographic image by the uniform volume to calculate a total volume. The spherical fill process can include identifying areas of overlap between the virtual spheres; determining a volume of the areas of overlap; and subtracting the volume of the areas of overlap from the total volume.

The convex hull process can include a computation of minimum convex sets that contain all of the points in the area of fluid in the three-dimensional sonographic image. The triangulation process can include a calculation of a minimum number of virtual triangles that make up a Euclidian space of points within the area of fluid in the three-dimensional sonographic image.

The receiving of data from the ultrasound transducer, the generating of the three-dimensional sonographic image with the data from the ultrasound transducer, the identifying of the body cavity in the three-dimensional sonographic image, the identifying of the area of fluid in the body cavity in the three-dimensional sonographic image, and the calculating of the volume of the area of fluid using the three-dimensional sonographic image and at least one of the stacked crescents process, the spherical fill process, the convex hull process, and the triangulation process can be repeated to generate sequential three-dimensional data sets. The sequential three-dimensional data sets can be compared to derive changes in volume. The changes in volume can be divided over elapsed time to estimate a rate of change in fluid (i.e., hemorrhage).

Figure 2:
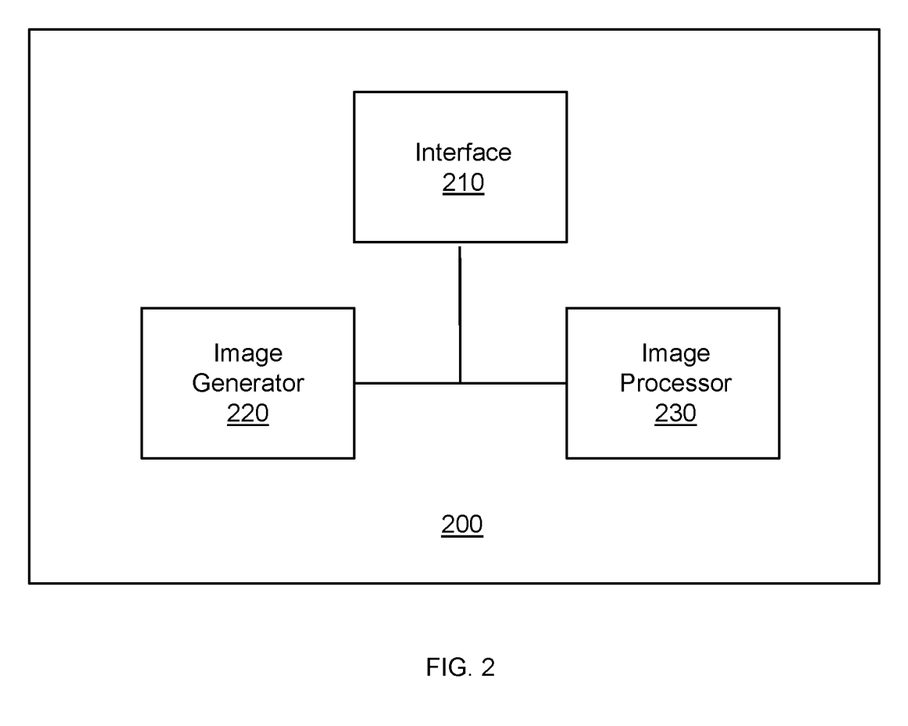
FIG. 2 illustrates a system to measure fluid within a body cavity according to an embodiment of the invention.

FIG. 2 illustrates a system to measure fluid within a body cavity according to an embodiment of the invention. An interface 210 can be configured to receive data from an ultrasound transducer. An image generator 220 connected to the interface 210 can be configured to generate a three-dimensional sonographic image from the data from the ultrasound transducer. An image processor 230 connected to the image generator 220 can be configured to identify the body cavity in the three-dimensional sonographic image, identify an area of fluid in the body cavity in the three-dimensional sonographic image, and calculate a volume of the area of fluid using the three-dimensional sonographic image and a stacked crescents process, a spherical fill process, a convex hull process, and/or a triangulation process.

The image processor 230 can be configured to divide the area of fluid in the three-dimensional sonographic image into stacked segments; identify crescents in the three-dimensional sonographic image, wherein each crescent is a non-overlapping area of two partially overlapping segments; calculate an area of each crescent; and sum the areas of the crescents.

The image processor 230 can be configured to virtually fill the area of fluid in the three-dimensional sonographic image with virtual spheres having a uniform volume; identify a minimum number of virtual spheres required to fill the area of fluid in the three-dimensional sonographic image; and multiply the number of virtual spheres required to fill the area of fluid in the three-dimensional sonographic image by the uniform volume to calculate a total volume. The image processor 230 can be configured to identify areas of overlap between the virtual spheres; determine a volume of the areas of overlap; and subtract the volume of the areas of overlap from the total volume.

The image processor 230 can be configured to compute minimum convex sets that contain all of the points in the area of fluid in the three-dimensional sonographic image. The image processor 230 can be configured to calculate a minimum number of virtual triangles that make up a Euclidian space of points within the area of fluid in the three-dimensional sonographic image.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium is a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3:
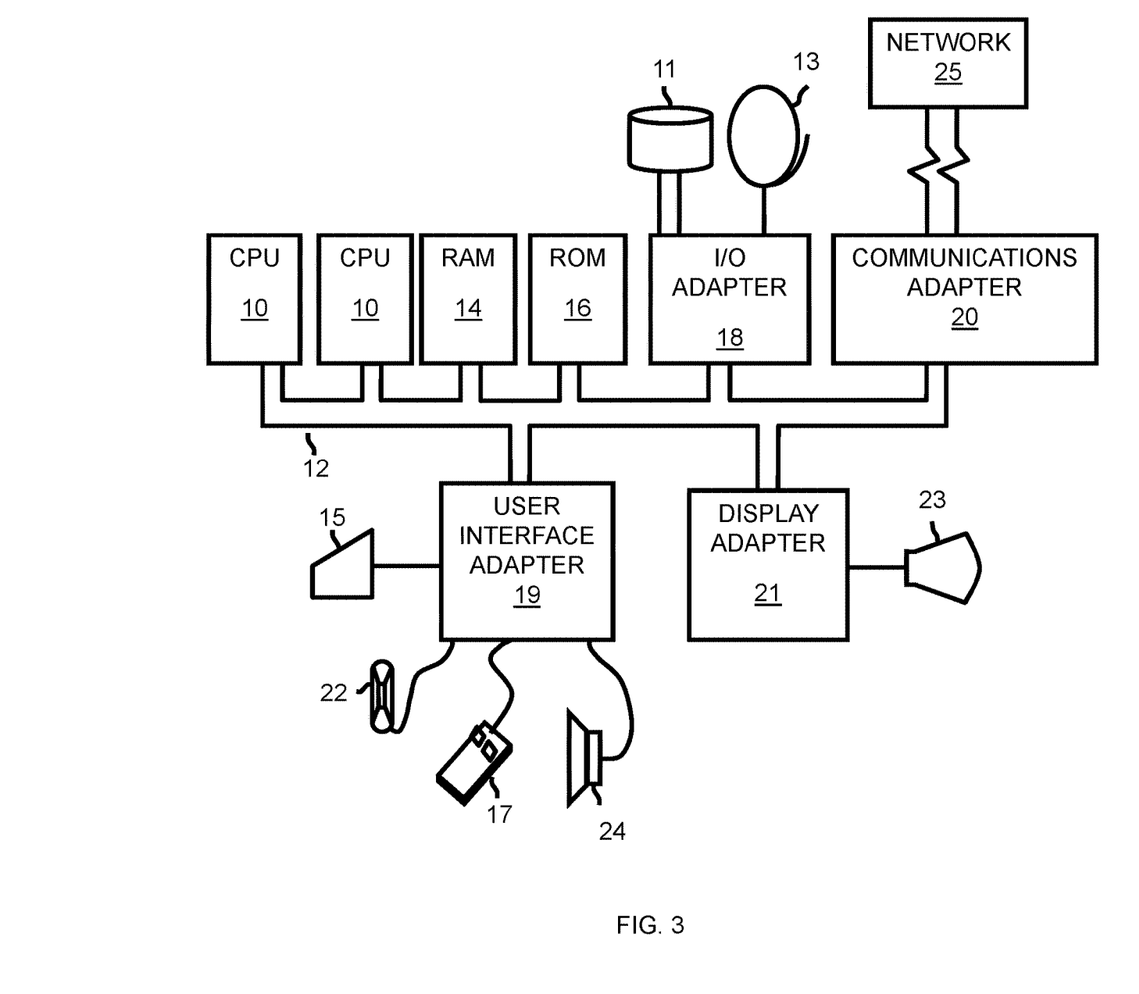
FIG. 3 illustrates a computer program product to measure fluid within a body cavity according to an embodiment of the invention.

Referring now to FIG. 3, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

At least one embodiment of the invention provides a three-dimensional ultrasound system with automated volume acquisition that is faster than two-dimensional ultrasound systems. The system can require minimal operator dependence, thus allowing for use by providers with no ultrasound experience. Three-dimensional ultrasound has been validated in the estimation of human bladder volume, which is ubiquitous in commercial use.

In at least one embodiment, latex balloons are filled with a known volume of water (e.g., 100 cubic centimeter (cc), 200 cc) and suspended in a mixture of gelatin and psyllium (e.g., 1500 cc water, 350 grams gelatin, 0.5 cups psyllium). A recipe can be created by increasing the ratio of psyllium in previously reported for soft tissue (breast) phantom. Morehouse H., Thaker H.P., and Persaud C., "Addition of Metamucil to Gelatin for a Realistic Breast Biopsy Phantom." J Ultrasound Med 2007; 26:1123-6. In at least one embodiment, five three-dimensional acquisitions and subsequent volume calculations were obtained for each model utilizing: a Phillips iU22 scanner, a 6-2 three-dimensional acquisition abdominal probe, and the AutoVolume feature of the Phillips QLAB software package for estimating volume.

Figure 4:
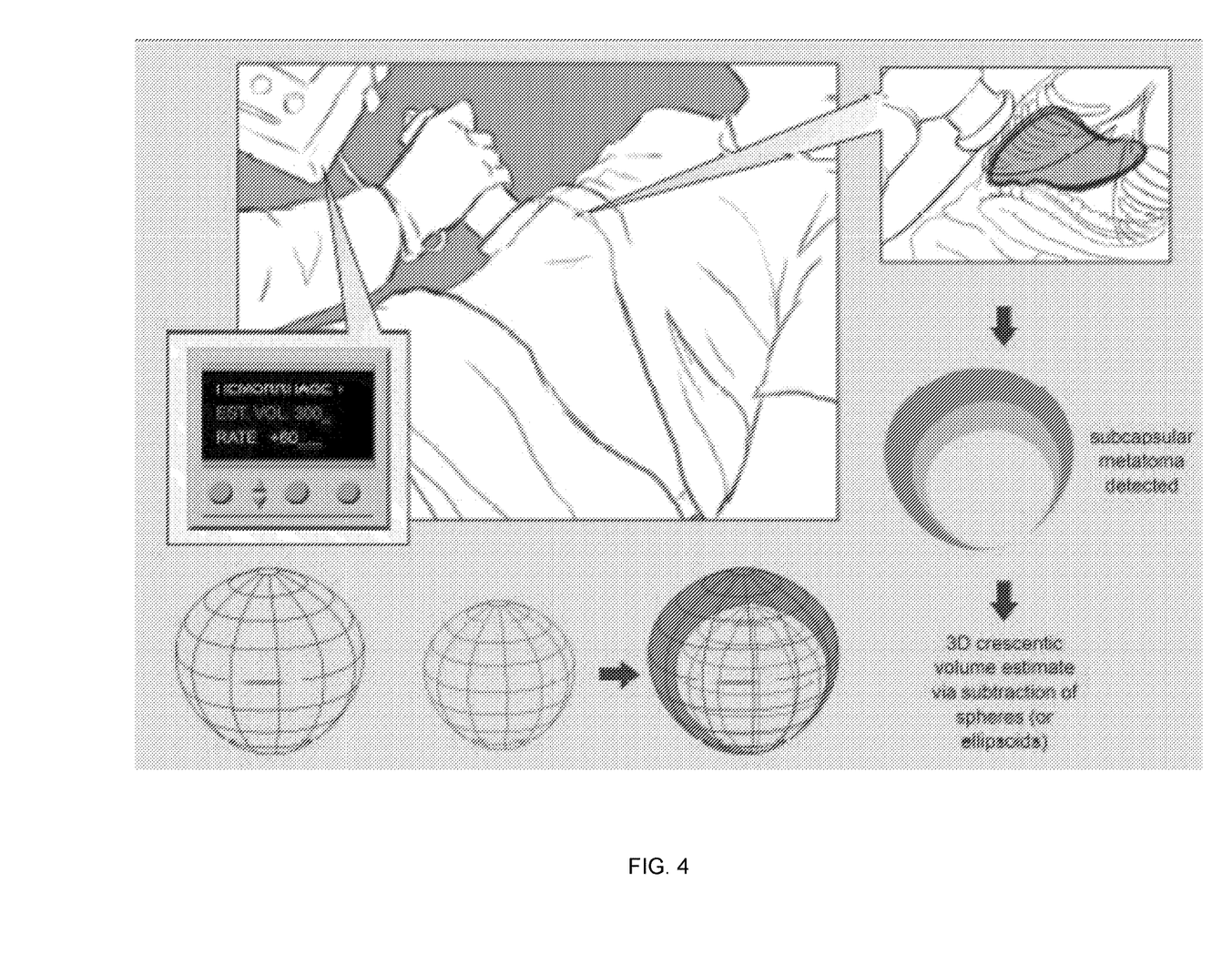
FIG. 4 is a diagram illustrating use of the system by a field medic according to an embodiment of the invention.

FIG. 4 is a diagram illustrating use of the system by a field medic according to an embodiment of the invention, where the system can alert the medic of a subcapsular hematoma. There are numerous methods of calculating the size of the visualized fluid volume. In this example, non-visualized portions of the collection are extrapolated by estimating the outer and inner arcs of the fluid collection and approximating to spheres. The overlapping volume of the spheres can then be subtracted from their total volumes. The difference in collection volumes divided by the time elapsed between measurements can yield an estimated rate of bleeding into a target fluid collection.

Figure 5:
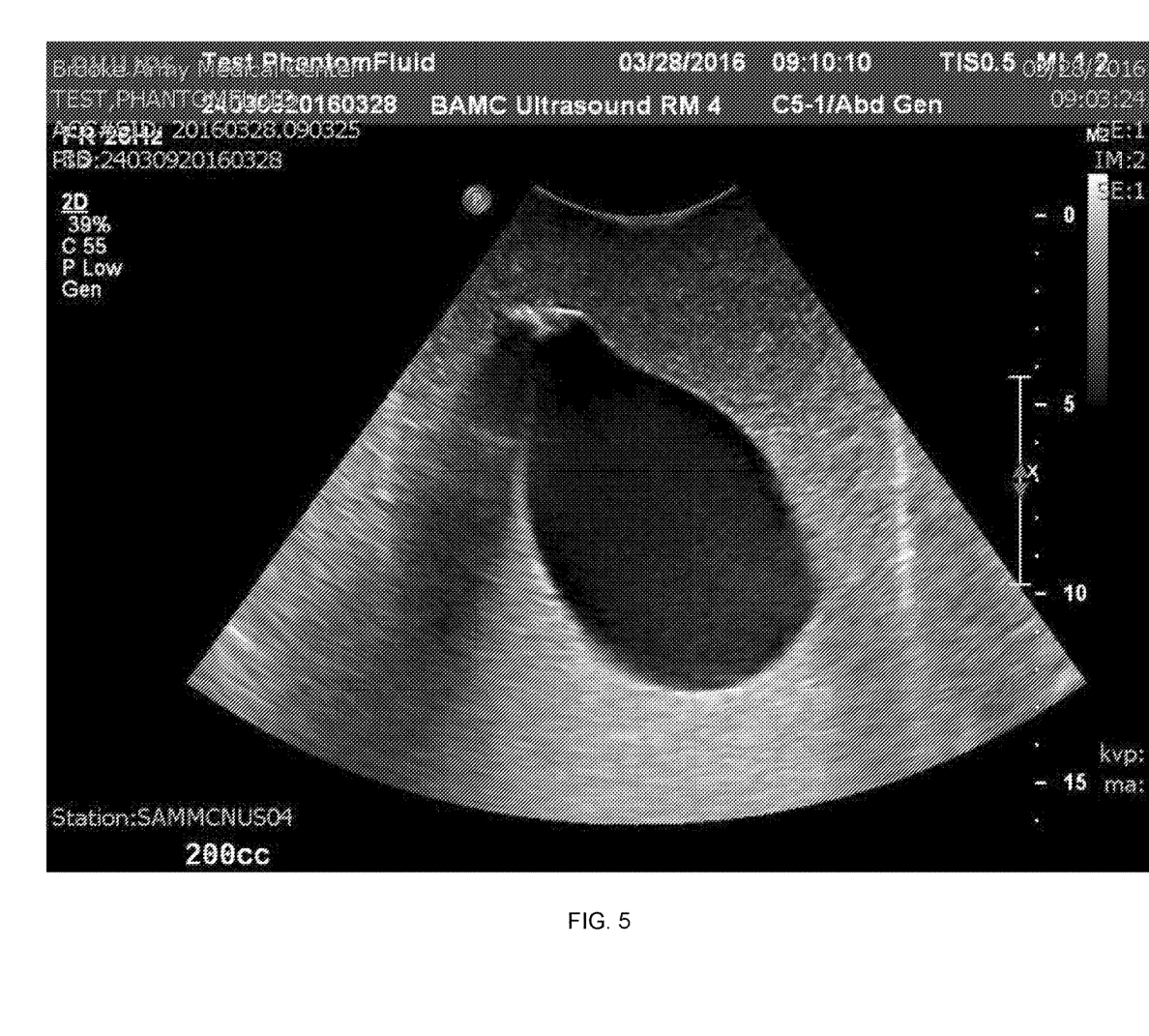
FIG. 5 illustrates a two-dimensional grayscale image of a 100 cc model according to an embodiment of the invention.
Figure 6:
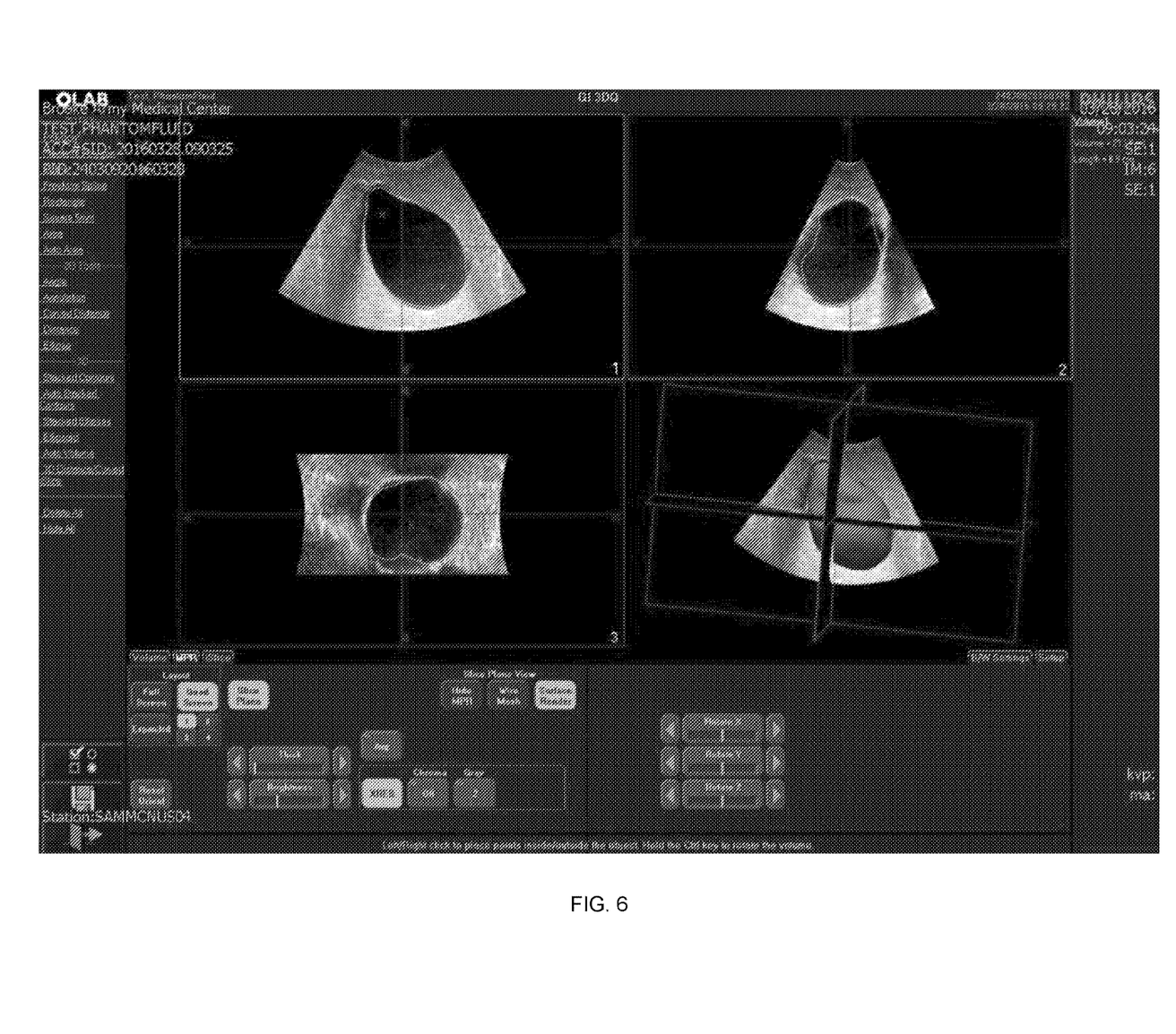
FIG. 6 illustrates a three-plane representation and volume fill according to an embodiment of the invention.

Exemplary volume estimates for the 100 cc balloon include: 100.4, 105.3, 100.9, 112.5, and 105.3. Exemplary volume estimates for the 200 cc balloon include: 213.8, 188.6, 201.2, 186.7, and 205.3. 100 cc model estimates were 105.7+/−4.2 (mean+/−SD); and, 200 cc model estimates were 199.1+/−11.4. The echogenicity of the model background may be comparable to a hepatic or splenic parenchyma. Three-dimensional volume sets can be best acquired when the target fluid collection is not directly subjacent to the transducer. Superficial acquisition can exclude the superficial portion of the collection. Sample images are illustrated in FIGS. 5 and 6, where FIG. 5 illustrates a two-dimensional grayscale image of a 100cc 100 cc model; and, FIG. 6 illustrates a three-plane representation and volume fill, Phillips QLAB. Three-dimensional ultrasound equipment and software can reproducibly characterize fluid collections of varying volumes within the low-cost phantom provided herein.

Phillips QLAB AutoVolume software may require user input to select the target volume (semi-automated). Untrained volunteers were not recruited to test the model due to the training required to operate the existing three-dimensional ultrasound software package. In at least one embodiment, model fluid collections were slightly irregular ellipsoids, whereas perihepatic and perisplenic fluid collections tend to be crescentic. Following the development of software optimized for the detection of non-spherical fluid collections, the shape of the phantom collection can also be modified to better simulate physiologic findings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

INDUSTRIAL APPLICABILITY

A system featuring methods of measuring fluid within a body cavity is provided. The provided systems and methods are particularly suited for generating a three-dimensional sonographic image from data from an ultrasound transducer and identifying an area of fluid in the body cavity in the three-dimensional sonographic image. The volume of the area of fluid is calculated using the three-dimensional sonographic image and a stacked crescents process, a spherical fill process, a convex hull process, and/or a triangulation process.

What is claimed is:

1. A method to measure fluid within a body cavity, said method including:

receiving data with an interface from an ultrasound transducer;

generating a three-dimensional sonographic image with an image generator connected to said interface, the three-dimensional sonographic image being generated from the data received from the ultrasound transducer;

identifying the body cavity in the three-dimensional sonographic image with an image processor connected to said image generator;

identifying an area of fluid in the body cavity in the three-dimensional sonographic image with said image processor; and calculating a volume of the area of fluid, the volume of the area of fluid being calculated using the three-dimensional sonographic image and a spherical fill process, and wherein said spherical fill process includes virtually filling the area of fluid in the three-dimensional sonographic image with virtual spheres having a uniform volume;

identifying a minimum number of virtual spheres required to fill the area of fluid in the three-dimensional sonographic image; and multiplying the number of virtual spheres required to fill the area of fluid in the three-dimensional sonographic image by the uniform volume to calculate a total volume.

2. The method according to claim 1, wherein said spherical fill process further includes:

identifying areas of overlap between the virtual spheres;

determining a volume of the areas of overlap; and subtracting the volume of the areas of overlap from the total volume.

3. The method according to claim 1, further comprising repeating said receiving of data from the ultrasound transducer, said generating of the three-dimensional sonographic image with the data received from the ultrasound transducer, said identifying of the body cavity in the three-dimensional sonographic image, said identifying of the area of fluid in the body cavity in the three-dimensional sonographic image, and said calculating of the volume of the area of fluid using the three-dimensional sonographic image and the spherical fill process to generate sequential three-dimensional data sets.

4. The method according to claim 3, further comprising comparing the sequential three-dimensional data sets to derive changes in volume.

5. The method according to claim 4, further comprising dividing the changes in volume over elapsed time to estimate a rate of change in fluid.

6. A system to measure fluid within a body cavity, said system including:

an interface configured to receive data from an ultrasound transducer;

an image generator connected to said interface, said image generator configured to generate a three-dimensional sonographic image from the data received from the ultrasound transducer; and an image processor connected to said image generator, said image processor configured to identify the body cavity in the three-dimensional sonographic image, identify an area of fluid in the body cavity in the three-dimensional sonographic image, and calculate a volume of the area of fluid using the three-dimensional sonographic image and a spherical fill process, and wherein said image processor is configured as part of the spherical fill process to virtually fill the area of fluid in the three-dimensional sonographic image with virtual spheres having a uniform volume;

identify a minimum number of virtual spheres required to fill the area of fluid in the three-dimensional sonographic image; and multiply the number of virtual spheres required to fill the area of fluid in the three-dimensional sonographic image by the uniform volume to calculate a total volume.

7. The system according to claim 6, wherein said image processor is further configured to:

identify areas of overlap between the virtual spheres;

determine a volume of the areas of overlap; and subtract the volume of the areas of overlap from the total volume.

8. The system according to claim 6, wherein said image generator is further configured to generate series of three-dimensional sonographic images; and said image processor is further configured to generate sequential three-dimensional data sets.

9. The system according to claim 8, wherein said image processor is further configured to compare the sequential three-dimensional data sets to derive changes in volume.

10. The system according to claim 9, wherein said image processor is further configured to divide the changes in volume over elapsed time to estimate a rate of change in fluid.

11. A non-transitory computer-readable medium having computer-readable instructions stored thereon which when executed by a computer cause the computer to perform a method for measuring fluid within a body cavity, said method comprising:

receiving data from an ultrasound transducer;

generating a three-dimensional sonographic image from the data received from the ultrasound transducer;

identifying the body cavity in the three-dimensional sonographic image;

identifying an area of fluid in the body cavity in the three-dimensional sonographic image; and calculating a volume of the area of fluid using the three-dimensional sonographic image and a spherical fill process, and wherein said spherical fill process includes virtually filling the area of fluid in the three-dimensional sonographic image with virtual spheres having a uniform volume;

identifying a minimum number of virtual spheres required to fill the area of fluid in the three-dimensional sonographic image; and multiplying the number of virtual spheres required to fill the area of fluid in the three-dimensional sonographic image by the uniform volume to calculate a total volume.

12. The non-transitory computer-readable medium according to claim 11, wherein said method further comprising repeating said receiving of data from the ultrasound transducer, said generating of the three-dimensional sonographic image with the data received from the ultrasound transducer, said identifying of the body cavity in the three-dimensional sonographic image, said identifying of the area of fluid in the body cavity in the three-dimensional sonographic image, and said calculating of the volume of the area of fluid using the three-dimensional sonographic image and the spherical fill process to generate sequential three-dimensional data sets.

13. The non-transitory computer-readable medium according to claim 12, wherein said method further comprising comparing the sequential three-dimensional data sets to derive changes in volume.

14. The non-transitory computer-readable medium according to claim 12, wherein said method further comprising dividing the changes in volume over elapsed time to estimate a rate of change in fluid.

* * * * *